United States Patent [19]
Buhler

[11] Patent Number: 5,803,870
[45] Date of Patent: Sep. 8, 1998

[54] EXERCISE MACHINE USING HEART RATE CONTROL FOR CARDIOPULMONARY INTERVAL TRAINING

[75] Inventor: Kirk A. Buhler, Corona, Calif.

[73] Assignee: Unisen, Inc., Tustin, Calif.

[21] Appl. No.: 643,745

[22] Filed: May 6, 1996

[51] Int. Cl.[6] .................................................. A63B 21/005
[52] U.S. Cl. .......................... 482/8; 482/1; 482/3; 482/9; 482/54; 482/900
[58] Field of Search ............................... 482/1–9, 54, 57, 482/900–902

[56] References Cited

U.S. PATENT DOCUMENTS

| 5,067,710 | 11/1991 | Watterson et al. | 482/64 |
| 5,462,504 | 10/1995 | Trulaske et al. | 482/7 |
| 5,527,239 | 6/1996 | Abbondanza | 482/3 |

FOREIGN PATENT DOCUMENTS

| 0 255 621 A | 2/1988 | European Pat. Off. . |
| 0 379 227 A | 7/1990 | European Pat. Off. . |

Primary Examiner—Richard J. Apley
Assistant Examiner—Glenn E. Richman
Attorney, Agent, or Firm—Knobbe, Martens, Olson & Bear, LLP

[57] ABSTRACT

Cardiopulmonary interval training between a user high target heart rate and a user low target heart rate is obtained with an exercise apparatus by increasing the load of the exercise apparatus at a first predetermined rate until either the maximum machine load is obtained or the high target heart rate. When this event occurs, the load can then be maintained at a fixed level for a predetermined time. Thereafter, the load is decreased until the low target heart rate is obtained, or the user-set exercise duration expired. The heart rate of the user is continuously monitored during the exercise. In the event that measurement of a valid heart signal is lost at any time, any increase or decrease of the load of the exercise apparatus is terminated until a valid heart rate signal is reacquired. In the case when an exercise apparatus is a treadmill, the load can be varied by increasing or decreasing both the speed adjustment and the elevation adjustment of the treadmill. In the preferred embodiment, the speed is first adjusted until a user-set maximum speed is obtained and thereafter the elevation is adjusted in order to obtain the load variations toward or from the high and low target heart rates. The exercise may be repeated between the low and high target heart rates to provide cardiopulmonary interval training.

23 Claims, 2 Drawing Sheets

EXERCISE MACHINE USING HEART RATE CONTROL FOR CARDIOPULMONARY INTERVAL TRAINING

BACKGROUND OF THE INVENTION

1. Field of the Invention

The invention relates to the field of exercise equipment utilizing interval training based on heart rate control.

2. Description of the Prior Art

The monitoring of heart rates for use on exercise equipment of all kinds, vertical bicycles, recumbent bicycles, steppers, treadmills, rowing machines and the like is well known. Typically, the exercise rate of the user is controlled according to a preset or calculated heart rate. The heart rate often is set based upon the user's age, weight and sex.

The user begins the exercise cycle by entering a warm-up period for a predetermined amount of time during which the exercise rate is not controlled by the actual monitored heart rate, other than perhaps a maximum limit. After the warm-up period, the user then increases the exercise rate or load, while the heart rate is monitored. The load may be varied according to various types of algorithms as the target heart rate is approached. Once the target heart rate is achieved, the load is thereafter varied to maintain the heart rate for a predetermined time or amount of exercise. Thereafter, a cool-down exercise period is performed at lower exercise rates or loads during which the heart rate is allowed to decrease.

However, it is appreciated by athletes that physical fitness training is more effectively reached by interval training. Interval training can in general be described as exercise at periodically higher and lower rates in a cyclic or repetitive pattern so that physical endurance is built up. Such interval training is based upon a cyclic pattern of physical exercise rates or exercise loads without regard to cardiopulmonary function, but is more directly concerned with the exercise and strengthening of skeletal muscle.

The same salutary benefits of interval training to skeletal muscle might be achievable in cardiopulmonary fitness if a means were provided by which heart activity, typically heart rate, could be used as the interval training parameter for controlling the exercise. Cardiopulmonary interval training becomes practical in the situation in which a stationary exercise machine can be utilized, such as a bicycle, stepper, treadmill, rowing machine and the like, where the exerciser remains fixed at a single location so that the cardiopulmonary function can be practically measured and the exercise environment responsively controlled in a manner to force the user to perform the cardiopulmonary regimen required by the interval training.

BRIEF SUMMARY OF THE INVENTION

The invention is a method for cardiopulmonary interval training with an exercise apparatus having a controllable load comprising the steps of determining a low target heart rate and determining a high target heart rate. A user's heart rate is measured. The load provided by the exercise apparatus is increased to the user while the user's heart rate is simultaneously measured. Increase of the load is limited by the high target heart rate. The load provided by the exercise apparatus to the user is decreased while simultaneously measuring the user's heart rate. Decrease of the load is limited by the low target heart rate. As a result, interval training is obtained between the high and low target heart rates. In the illustrated embodiment the low target heart rate and high target heart rate separated by at least 5 beats-per-minute.

The load is increased at a first predetermined rate and decreased at a second predetermined rate. The method further comprises the step of maintaining the load at a maximum for a predetermined time when the high target heart rate is achieved. The load is maintained at a maximum magnitude for a predetermined period of time whenever the maximum load of the exercise apparatus is reached.

In another embodiment the method further comprising maintaining the load for a predetermined time whenever the high target heart rate or maximum possible load of the exercise apparatus has been obtained, whichever occurs first.

The method further comprises temporarily terminating increase of the load whenever measurement of the user's heart rate is lost and thereafter continuing to increase the load when the user's heart rate is reobtained.

In the illustrated embodiment the exercise apparatus is a treadmill having both speed and elevation adjustments and further comprises the step of determining a maximum speed at which the user will exercise upon the treadmill. The load is increased by increments in the speed adjustment until the maximum speed is achieved. The method further comprises increasing the elevation after the maximum speed has been achieved. If the high target heart rate has not been achieved by increments in the elevation adjustments. The method further comprises maintaining the treadmill at the maximum speed and a maximum elevation for a predetermined time if the high target heart rate has not been achieved. Otherwise, any increase of speed or elevation adjustment is terminated when the high target heart rate has been achieved, whichever has not previously been reached. Decreasing the load comprises first decreasing the elevation adjustment of the treadmill, if any, at a predetermined rate and thereafter decreasing the speed adjustment of the treadmill until the low target heart rate is obtained. In any case the method terminates increasing or decreasing the load whenever the user heart rate measurement is no longer obtained.

The steps of increasing the load and decreasing the load are cyclically repeated to provide a multiple of training intervals.

The invention is also characterized as an apparatus for providing cardiopulmonary interval training comprising a controllable load for receiving work from a user, a coupling mechanism, like a treadmill belt, for transferring work from the user into the load, and a heart monitor for measuring the heart rate of the user. A controller is coupled to the load for receiving a high target heart rate input and a low target heart rate input from the user. The controller receives measured heart rate signals from the heart monitor, and controls the load according to the inputs and to the measured heart rate signal to increase the load at a first predetermined rate without exceeding the high target heart rate and thereafter to decrease the load at a second predetermined rate without falling below the low target heart rate. As a result, cardiopulmonary interval training according to user inputs is obtained.

The controller increases the load until the high target heart rate or maximum load capable for the apparatus is obtained and thereafter maintains the load at a fixed level for a predetermined amount of time. The controller maintains the load at its current value whenever the heart monitor ceases to obtain valid measured heart rate signals. The coupling mechanism is preferably a treadmill and the load has a speed adjustment and elevation adjustment of the treadmill. The controller increases or decreases the speed adjustment of the treadmill after a user-defined maximum of speed is obtained and thereafter increases or decreases set elevation adjustment of the treadmill only after the user-maximum speed has been achieved.

The invention and its various embodiments may be better visualized by now turning to the following drawings wherein like elements are referenced by like numerals.

Figure 1:
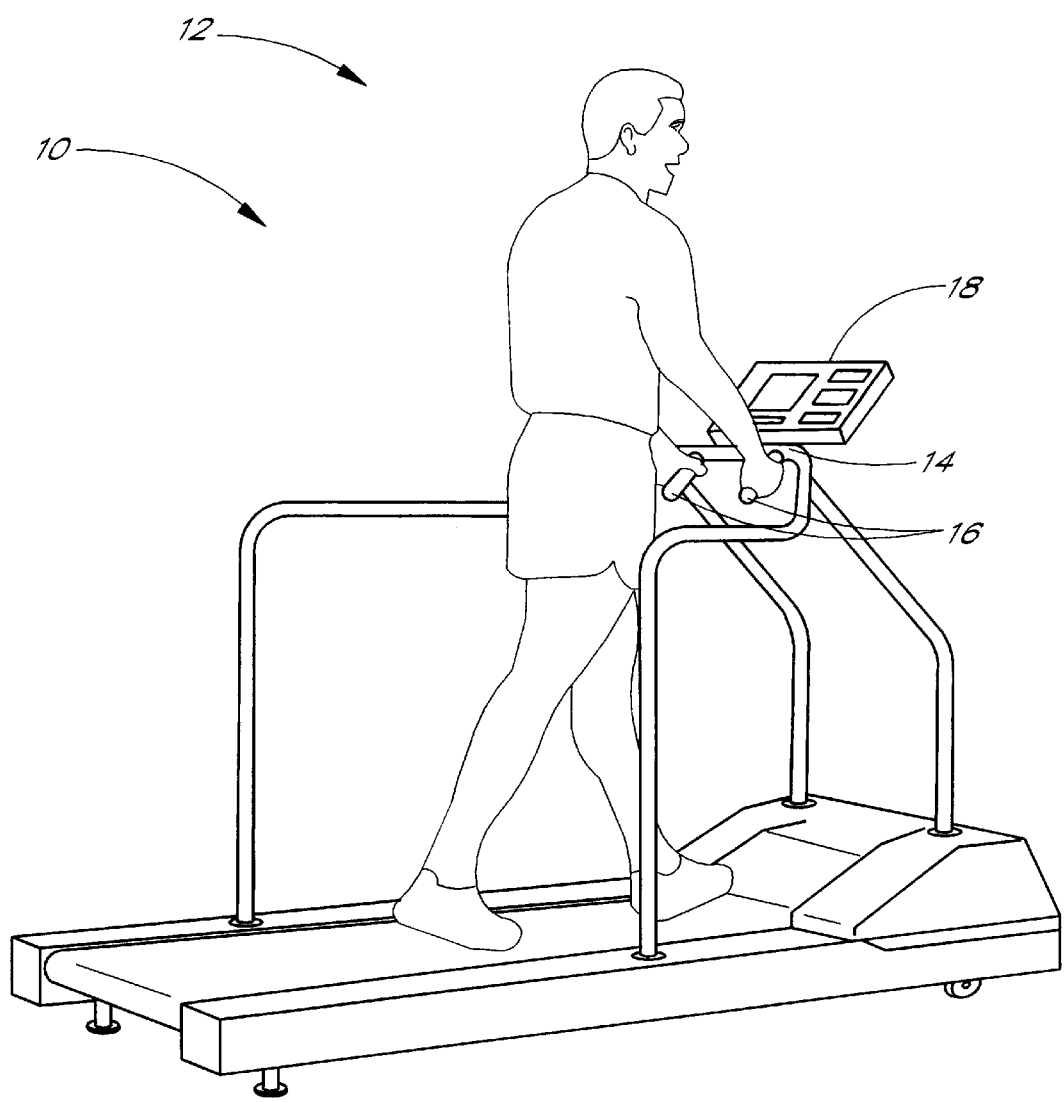
FIG. 1 is a diagrammatic depiction of a user on a treadmill practicing the interval training of the invention.

The illustrated embodiment having been generally illustrated in the foregoing Figures can now be understood in connection with the following detailed description.

DETAILED DESCRIPTION OF THE PREFERRED EMBODIMENTS

Cardiopulmonary interval training between a user high target heart rate and a userset low target heart rate is obtained with an exercise apparatus by increasing the load of the exercise apparatus at a first predetermined rate until either the maximum machine load is obtained or the high target heart rate. When this event occurs, the load is then maintained at a fixed level for a predetermined time. Thereafter, the load is decreased until the low target heart rate is obtained, or the user-set exercise duration expired. The heart rate of the user is continuously monitored during the exercise. In the event that measurement of a valid heart signal is lost at any time, any increase or decrease of the load of the exercise apparatus is terminated until a valid heart rate signal is reacquired. In the case when an exercise apparatus is a treadmill, the load can be varied by increasing or decreasing both the speed adjustment and the elevation adjustment of the treadmill. In the preferred embodiment, the speed is first adjusted until a user-set maximum speed is obtained and thereafter the elevation is adjusted in order to obtain the load variations toward or from the high and low target heart rates. The exercise may be repeated between the low and high target heart rates to provide cardiopulmonary interval training.

The invention is directed to a method for controlling an exercise machine to establish a lower and upper heart rate limit and to make adjustments to the machine on a periodic basis in order to oscillate the user's heart rate between the two limits until the user completes a predetermined exercise set. It is to be understood that the type of exercise and the exercise equipment, and the type of load and means by which such load may be provided to the user is entirely arbitrary, limited only by consistency with the following teachings. Therefore, upright or recumbent bicycles, steppers, treadmills, rowing machines, weight lifting apparatus and exercise equipment of all and any type by which a user in any condition, fit or handicapped, may be elevate his or her cardiopulmonary function, is contemplated expressly as within the scope of the invention. In the illustrated embodiment a treadmill using an alternator loaded by a resistive load is assumed by example, but not by way of limitation.

Further, the means by which the heart rate is monitored is also not restricted in any particular manner as long as it is consistent with the teachings presented here. For example, the heart rate may be monitored through any type of pressure transducer, which detects pulse or respiration rates, or both, attached or coupled at any place on the user's body or by electrophysiological means, whereby the electrocardiographic signal from the user is communicated continuously or intermittently to the control unit of the machine.

For example, FIG. 1 is a highly diagrammatic depiction of a treadmill 10 upon which a user 12 grasps a handbar 14 on which there are conventional electrodes 16 from which user's heart 12 can be detected. Any contact or noncontact heart rate monitoring device or methodology may be used. Treadmill 10 is controlled by control circuitry contained within an input/output and display unit 18. Typically, treadmill 10 can be operated in a plurality of different exercise modes of which the interval training mode is one.

Figure 2:
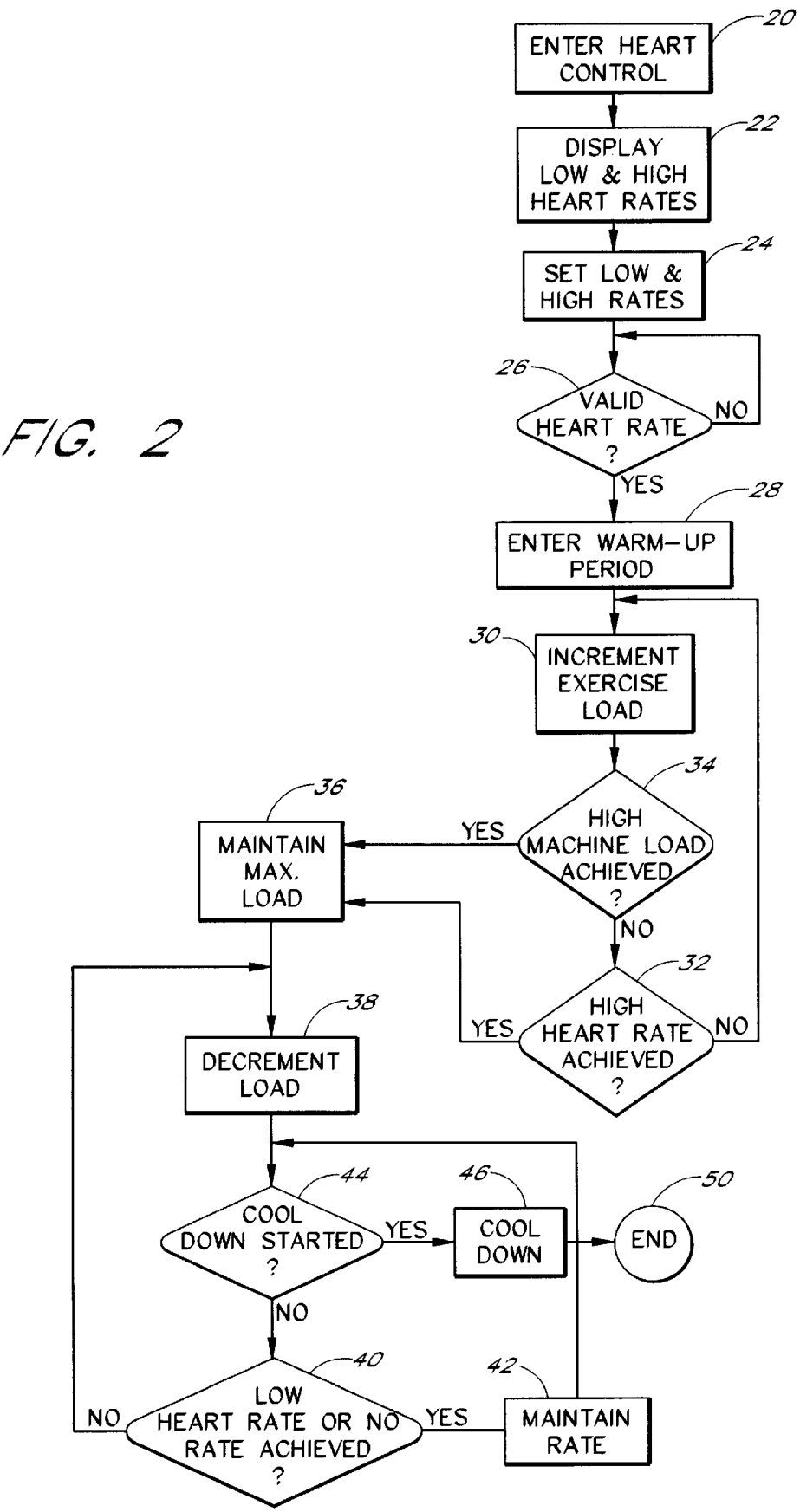
FIG. 2 is a block diagram of the methodology of the invention by which the exercise device of FIG. 1 is controlled.

The interval heart rate control mode can be entered at any time by pressing a heart key at step 20, illustrated in the flow diagram of FIG. 2. The heart key is typically user accessible and displayed immediately in front of user 12 on console 18. When the heart key is pressed, display 18 will show a low and a high value for heart rate, typically in beats-per-minute, such as symbolically displayed in step 22. For example, low and high heart rates may be set between minimum and maximum, such as a minimum of 80 beats-per-minute and a maximum of 210 beats-per-minute. Within the range of permissible parameters, as may be determined by the mechanical performance of treadmill 10, the low and high values are selected by user 12 either by hitting an increment or decrement key on console 18, or entering a specific number on a keypad which may be provided, as symbolized in step 24.

For example, a low value may flash at a periodic rate such as 2 Hz for a predetermined period of time, such as 10 seconds, during which user 10 may input a different value than the default value, accept the last value entered in the machine, or a value retrieved from memory based on user selection. Thereafter, the high heart rate value will flash for 10 seconds, allowing user 12 the option of setting the high heart rate in the same manner.

In the illustrated embodiment, the method will make exercise changes only when valid heart rate information is received. If control console 18 stops receiving information, no changes are made in control until a valid heart rate is detected. Any means now known or later devised by which heart rate signals can be discriminated from other signals and noise may be utilized. In the illustrated embodiment, heart rate signals are uniquely identified by the electrical signal strength or signal nature across hand electrodes 16. Once a valid heart rate signal is detected at step 26, the method continues from the control point when valid heart rate information was last obtained. In the illustrated embodiment, no prompting is made to exerciser 12 to reestablish heart monitoring, although communication with the user regarding the receipt or not of valid heart rate is entirely within the scope of the invention.

At this point, the warm-up period is entered at step 28 wherein exercise load, work level or exercise rate starts at the minimum machine setting predetermined for treadmill 10. This minimum setting may, but need not necessarily, be below the low setting set at step 24. While the heart rate information is being monitored, treadmill 10 will increase the load or work level at a periodic rate until the high heart rate target set in step 24 is achieved as determined at step 32. For example, every 30 seconds, the load or work level of treadmill 10 may be increased by five percent, or some other increment, until the high target heart rate is achieved, or alternatively, until the highest work load within the range of treadmill 10 is reached whichever may be first.

If treadmill 10 reaches its maximum load or work level and user 12 has still not achieved the high target heart rate, as determined at step 34, treadmill 10 will maintain the maximum load for a predetermined time at step 36, for example 30 seconds, after which the load will begin to be decremented by predetermined increments at step 38 until the low heart rate is achieved as determined at step 40. When treadmill 10 transitions from the high heart rate to the low target heart rate, decrementing steps 38 are made every 30 seconds or other interval and rate. This cycle is continued until the low target heart rate is achieved after which the low rate is maintained at step 42 or until cool-down period has started as determined at step 44. If the timed program point for cool-down has been achieved, then the heart rate is ceased to be monitored at step 46 and the cool-down exercise phase is implement at step 46 as is conventional.

Alternatively, step 40 will determine if no heart rate is sensed within a predetermined timed period, and if so, this event will also be treated as the achievement of low heart rate, resulting in the maintenance of the then-achieved rate at step 42 until cooldown down is initiated as determined at step 44 and implemented at step 46. This then represents one interval training cycle, which may then repeated a number of times, either predetermined by program control or as selected by user 12.

The embodiment of FIG. 2 has been described generically in terms of machine load. In the case of a bicycle or stepper, for example, the machine load will be comprised of the actual physical force required to step or peddle the device. The speed of stepping or peddling is determined by the user in response to the load limited by the achieved heart rate as described.

In another embodiment, machine load can be comprised of a plurality of parameters such as both speed and elevation, as is the case in a treadmill. In this case, step 34, for example, is comprised of a two-step determination. First, a determination is made whether or not treadmill 10 has reached a preset or user set high speed limit. The user, by personal preference or age, may wish to limit the speed of the treadmill to a comfortable or desired rate. If the high target heart rate is not achieved at step 32, then on the next cycle through step 34, the load is increased, not by increasing the speed, which has presumably reached the high speed limit, but by increasing the elevation of the treadmill, for example by two percent inclination increments on each cycle through step 34.

In the case where the load has been increased by increasing elevation of treadmill 10, then in the decrement step 38, the load is first decreased by decreasing elevation inclination before speed is decreased. Thereafter, speed is decreased by a predetermined increment, such as 0.5 miles-per-hour until the load heart rate is achieved at step 40, or no heart rate is sensed. In the case of a plurality of parameters for adjustment of machine load, neither parameter will be changed unless valid heart information is received.

Consider for example, a specific embodiment. For example in FIG. 2, after selecting heart rate control at step 20, the user will be prompted to enter his or her weight, age and a duration time for their exercise with time-outs reverting to a track display in the event that any of this input parameters fail to be provided within a predetermine time. The track display is a symbolic depiction of a track around which the exercisers output is measured in laps. The default low heart rate is then determined, for example, by the formula 220−age×0.6. Exerciser 12 either accepts the default low rate or enters a new rate with a distinctive feedback beep for every change in the heart rate entered with, for example, 5 beats-per-minute being a minimum increment. The maximum rate, for example, of 199 beats-per-minute will be permitted with a second distinguishable tone provided as feedback to the user if an out-of-range value is attempted, in which case, the last value for the low target heart rate will be entered as a default. The high rate is then set at the low rate, but incremented at 5 beats-per-minute as a default value. In this case, the exerciser will then be cycled between the low and high interval targets within a narrow band of 5 beats-per-minute.

User 12 has the option to increase this heart rate range according to personal training experience and goals to any difference permitted between the low target rate and the maximum permitted rate of 199 beats-per-minute. Again, the first tone is provided with every change of the heart rate as the high target rate is set, with a second distinctive tone provided when an out-of-range value is attempted to be entered. If an out-of-range value is entered as the high target rate, then the last high target rate entered will appear as a default.

The high and low heart rates having thus been set, console 18 will then prompt for a high speed limit. As stated, the high speed limit can be arbitrarily set within the range of the machine at predetermined intervals and is arbitrarily selected by the users according to their own comfort and discretion. Therefore, having a high speed limit and low and high target rates set into the device, the process then begins with detection of a valid heart rate at step 26 and a warm-up at step 28, followed by the interval exercise described above. The warm-up period of step 28 may be practiced by accelerating the treadmill belt by 0.5 mile-per-hour increments through an predetermined time interval until 60 percent of the high speed limit set by user 12 has been reached. If valid heart rate information is not obtained at this point, console 12 will provide a display showing that it is still looking for a valid heart rate, and if within 20 seconds no heart rate is provided, display a message to the user that heart rate signal has failed to be detected and all further adjustments to speed or elevation of treadmill 10 will be stopped until a valid heart rate is obtained.

Once treadmill 10 does obtain a valid heart rate and warm-up period 28 completed according to conventional parameters, speed is increased every 30 seconds by 5 percent until the high speed target or high heart rate target is achieved. If the high speed has been achieved, but the high target rate has not been achieved, treadmill 10 will increase elevation by 2 percent grade inclination every 30 seconds until it reaches its highest elevation, or the high heart target rate has been received. At that point, the highest elevation and highest set speed will be maintained at step 36 for 30 seconds, and thereafter adjustments made to achieve the low heart target rate. Treadmill 10 then makes adjustments every 30 seconds by decreasing elevation by 2 percent grade decrements to zero elevation and then decreasing the speed by 0.5 mile-per-hour until the low heart target rate is achieved or the duration time limit reached. Decrementation continues until the cool-down period begins or no heart rate is sensed. Loss of heart rate will result in the display first searching for heart rate, and if no heart rate information is found, treadmill 10 will make no further adjustments in speed or elevation until it receives valid heart rate signals. The speed and elevation adjustments will continue as described, however, once valid heart rate information is established. Periodically, the methodology allows adjustment of the heart rate during exercise. If the user does not make an adjustment of the low or high limits, then the last set values will then be used as a default.

In the illustrated embodiment, the decrementation of the load will in the last 60 seconds of the program slow the belt to 60 percent of the speed achieved just prior to the last 60 seconds and lower the elevation to zero degrees regardless of the load point reach just prior to the 60 second point. Thereafter, the 30 second cool-down period begins, after which the belt comes to a stop and there is a summary of information displayed on console 18, such as the interval target heart rates with congratulatory or encouraging prompts to the user for a successful workout.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

I claim:

1. A method for cardiopulmonary interval training with an exercise apparatus having a controllable load comprising:

determining a first target heart rate for a user and a first load setting which corresponds to the first target heart rate for the user;

determining a second target heart rate for the user and a second load setting which corresponds to the second target heart rate for the user;

measuring the user's heart rate as the user exercises on the exercise apparatus; and varying the load from the first load setting toward the second load setting at a predetermined rate or over a predetermined time period until the second target heart rate is achieved, said predetermined rate or predetermined time period being dependent on the difference between the first and second load settings corresponding to the first and second target heart rates for the user;

whereby the predetermined rate or predetermined time period varies from user to user depending upon the physical conditioning of the user as determined by the first and second load settings.

2. The method of claim 1 wherein said load is increased at a first predetermined rate.

3. The method of claim 1 wherein said load is decreased at a second predetermined rate.

4. The method of claim 1, further comprising maintaining said load at a maximum setting for a second predetermined period of time when said second target rate is achieved.

5. The method of claim 1, further comprising maintaining said load at a maximum setting for a second predetermined period of time when a maximum load of the exercise apparatus is achieved.

6. The method of claim 1, further comprising maintaining said load for a second predetermined period of time when said second target rate or a maximum load of the exercise apparatus is achieved, whichever occurs first.

7. The method of claim 1, further comprising temporarily terminating varying said load whenever measurement of said user's heart rate is lost and thereafter continuing to vary said load when said user's heart rate is reobtained.

8. The method of claim 1, wherein the exercise apparatus is a treadmill having a first load setting determined by both speed and elevation adjustments and further comprising determining a maximum speed at which said user will exercise upon said treadmill, said load being increased by increments in said speed adjustment until said maximum speed is achieved.

9. The method of claim 8, further comprising increasing said load after said maximum speed has been achieved if said second target heart rate has not been achieved, by incrementally increasing said elevation adjustments.

10. The method of claim 9 further comprising maintaining said treadmill at said maximum speed and a maximum elevation for a second predetermined period of time if said second target heart rate has not been achieved, otherwise terminating increase of speed or elevation adjustment when said second target heart rate has been achieved.

11. The method of claim 9, where decreasing said load comprises first decreasing said elevation adjustment of said treadmill, if any, at a predetermined rate and thereafter decreasing said speed adjustment of said treadmill until said first target heart rate is obtained.

12. The method of claim 8 further comprising terminating increasing or decreasing said load whenever said user heart rate measurement is no longer obtained.

13. The method of claim 1 wherein said first and second target heart rates are separated by a predefined number of beats-per-minute.

14. The method of claim 1 where said steps of increasing said load and decreasing said load are cyclically repeated to provide a multiple of training intervals.

15. An apparatus for providing cardiopulmonary interval training comprising:

a controllable load for determining work output from a user, a heart monitor for measuring the heart rate of said user; and a controller coupled to said load for receiving information representative of a second target heart rate and a first target heart rate for said user and for receiving measured heart rate signals from said heart monitor, said controller varying the load from the first load setting toward the second load setting at a predetermined rate or over a predetermined time period until the second target heart rate is achieved, said predetermined rate or predetermined time period being dependent on the difference between the first and second load settings corresponding to the first and second target heart rates for the user;

whereby cardiopulmonary interval training is obtained.

16. The apparatus of claim 15 where said controller increases said load until said second target heart rate or maximum load capable for said apparatus is obtained and thereafter maintains said load at a fixed level for a predetermined period of time.

17. The apparatus of claim 15 wherein said controller maintains said load at its current value whenever said heart monitor ceases to obtain valid measured heart rate signals.

18. The apparatus of claim 15 wherein said exercise machine is a treadmill and said load has a speed adjustment and elevation adjustment mechanism.

19. The apparatus of claim 18 wherein said controller increases or decreases said speed adjustment of said treadmill after a user-determined maximum of speed is obtained and thereafter increases or decreases set elevation adjustment of said treadmill only after said user-maximum or device minimum speed has been achieved.

20. The method of claim 1, further comprising maintaining said load at a minimum setting for a third predetermined period of time when said first target rate is achieved.

21. The method of claim 1, further comprising maintaining said load at a minimum setting for a third predetermined period of time whenever the minimum load of the exercise apparatus is achieved.

22. The method of claim 1, further comprising maintaining said load for a third predetermined period of time whenever said first target rate or a minimum load of the exercise apparatus is achieved, whichever occurs first.

23. The apparatus of claim 15 where said controller increases said load until said first target heart rate or minimum load capable for said apparatus is obtained and thereafter maintains said load at a fixed level for a predetermined period of time.

* * * * *